US007201910B2

(12) United States Patent
Griffiths et al.

(10) Patent No.: US 7,201,910 B2
(45) Date of Patent: Apr. 10, 2007

(54) NUCLEIC ACID AND AMINO ACID SEQUENCES OF INFECTIOUS SALMON ANAEMIA VIRUS AND THEIR USE AS VACCINES

(75) Inventors: Steven G Griffiths, Fredericton (CA); Rachael J Ritchie, Hanwell (CA)

(73) Assignees: Novartis AG, Basel (CH); Ottawa Health Research Institute, Ottawa (CA)

( * ) Notice: Subject to any disclaimer, the term of this patent is extended or adjusted under 35 U.S.C. 154(b) by 0 days.

(21) Appl. No.: 11/083,800

(22) Filed: Mar. 18, 2005

(65) Prior Publication Data

US 2005/0261227 A1 Nov. 24, 2005

Related U.S. Application Data

(62) Division of application No. 10/049,086, filed as application No. PCT/GB00/02976 on Aug. 7, 2000, now Pat. No. 6,919,083.

(30) Foreign Application Priority Data

| Aug. 7, 1999 | (GB) | ............................... | 9918588.6 |
| Mar. 11, 2000 | (GB) | ............................... | 0005848.7 |
| Mar. 21, 2000 | (GB) | ............................... | 0006674.6 |

(51) Int. Cl.
*A61K 39/145* (2006.01)

(52) U.S. Cl. .......................... 424/209.1; 514/2; 514/44

(58) Field of Classification Search ............ 424/209.1; 514/2, 44
See application file for complete search history.

(56) References Cited

U.S. PATENT DOCUMENTS 6,471,964 B1 10/2002 Biering et al.

FOREIGN PATENT DOCUMENTS

| WO | WO/ 00/72878 | 12/2000 |
| WO | WO 01/49712 | 1/2001 |
| WO | WO 01/66569 | 9/2001 |
| WO | WO/ 02/26784 | 4/2002 |

OTHER PUBLICATIONS

Colman, P.M., Effects of amino acid sequence changes on antibody-antigen interactions, Research Immunology, Jan. 1994, 145:33-36.*
Kibenge et al. "Antigenic Variation Among Isolates of Infectios Salmon Anaemia Virus Correlates with Genetic Variation of the Viral Haemagglutinin Gene", Journal of General Virology, vol. 82, pp. 2869-2879, (2001).
Krossoy et al. "Cloning and Identification fo the Infectious Salmon Anaemia Virus Haemagglutinin" Journal of General Virology, vol. 82, pp. 1757-1765, (2001).
Rimstad et al. "Characterization of the infectious Salmon Anemia Virus Genomic Segment that Encodes the Putative Hemagglutinin", Journal of Virology, vol. 75, No. 11, pp. 5352-5356, (2001).
Griffiths et al., "Characterization of ISAV Proteins from Cell Culture", Diseases of Aquatic Organisms, vol. 45, pp. 19-24, (2001).
Mjaaland et al. "Genomic Characterization of the Virus Causing Infectious Salmon Anemia in Atlalntic Salmon (*Salmo salar* L.): an Orthomyxo-Like Virus in Teleost", Journal of Virology, vol. 71, No. 10, pp. 7681-7686, (1997).
Falk et al., Characterization of Infectious Salmon Anenia Virus, an Orthomyxo-Like Virus Isolated from Atlantic Salmon (*Salmo saler* L.) Journal of Virology, vol. 71, No. 12, pp. 9016-9023, (1997).
Ritchie et al, "Virus Genes", 22(3): pp. 289-297 (2001).

* cited by examiner

*Primary Examiner*—Stacy B. Chen
(74) *Attorney, Agent, or Firm*—E. Jay Wilusz

(57) ABSTRACT

The present invention provides the use of nucleic acid sequences and/or amino acid sequences in the preparation of a vaccine for the protection of fish against infectious salmon anaemia virus. Specifically, such vaccines contain at least one nucleic acid sequence which is derived from ISAV or synthetically prepared analogues thereof, or substantially homologous sequences. These nucleic acid sequences are transcripted and translated into peptide sequences which are incorporated into a vaccination strategy to induce and immune response to the surface antigens of ISAV and therefore ISAV itself. Therefore both the use of a vaccine against ISAV, and the incorporation of peptide sequences is herein described.

13 Claims, 10 Drawing Sheets

Figure 1: ISA2cd Nucleotide Sequence

```
caagatggat aacctccgtg aatgcataaa ccgcaaaaga agactacttg ccttaccaga    60
tgttcctgaa acttcggatg cctttctaag tgatttgaga catctataca tgtgtgttgc   120
tttctgtgat caacacaaaa ccactggaga cgaatcaaga ttcaccaacc tggaattact   180
tgaccaagat gaagcactag gtgcccaaag agcttttgaa gccaaacatg aataaaagg    240
aggttcttta ggagacgttc ttgaccatga actgaaaaag gtcattgaat ttacttttac   300
ttctggaagt ttgtatattg ccgaacaaag aaaaagaaag actcaagcag actcaataat   360
tgtgtgcgtt tcagaaggac ttaacgactt cagcgtatca cacggagtgc tagacatggg   420
acttgtggaa acaggggtga atgcagtaag agatttctgc acacaaaacg gaataccaat   480
gaagataaat caggtaggat ccacgagaac accaacaccg atcagcacat gcaaaatctc   540
tgaacaaata acacgacaga taaacagtac aattactgaa aggaaaatgg aaacagtact   600
ggcagcaatc gcaattaaac cagaactcaa actaactcag aaaggatgca gaccttgtaa   660
agaactagaa gatgaaaata ttctgtggat ggaccctcaa ttctgtgaaa ttgatgaaag   720
tttccttac agaggagggc catacggaa cttcctgcaa gaattgctgc ttacaaccaa    780
cgacgtagag accaacggga aagacagaga agaagtagta aagaagatac tggataacaa   840
ggcgttcacc gttgaaagtg gtgaatgcat aataacactt ccagacaaaa tgacttgttt   900
cggagaacag gagaagaaga gaccagcaac aatagacgaa gtgagaaccg caggagaaag   960
gtttgaacag agtgttaaac cgaaaccca aagatatgga aggttatcag acaaatggat  1020
ggagcttgaa aagtttatct ttactgcaag caaaacagaa gtggatactt tcctttctgt  1080
agggaccgaa agacttgagt cggttggagt gtgtgtcgga gctttacaca gagcgaccac  1140
aaccaggata attagaccta tgattcaagg agggaaatgt tgggggatga tgttcaaaac  1200
aaagtccaaa atgggagaca cgaggaagga aggatactgt cacgcaatca ttttcggaaa  1260
agggaagat aaatcaggac aaaacaagat gacaatgatg gggaaaacag tacattggca  1320
tctaagagta gttaagtcta aaggagactg gatggcgcaa caactctgtg caaacaaaag  1380
cagaatatgg gaacatgacc ctgagctagt aacagaagga gtgacagttc taatgacgcc  1440
ttttctcag aaaattgcca ccattagtag atggaggca atgaggttag acagcatgtt  1500
tcatgtttct agtgcctggc atcattcacc tgcgtgtgaa gctgcatcgg caatgctgag  1560
aaagtttgtg gagatagtac atgccatcaa ccagaaaaga gattggggtg ttgtggggag  1620
tatggaggac atggtgaagg aagtggagga aataggggag cacttgcaga cggcatgtga  1680
ttttagagtt tacaacatgt gcaaagcctt gattcagaaa attgcagtca gtacccaatg  1740
agtggttatt tacttgtaaa ttgttgtgtg tttgacgata tgtatttgtc gacgcggccg  1800
cggtcgacgc ggccgcgaat t                                            1821
```

Figure 2: ISA2cd Amino Acid Sequence

```
           1          11         21         31         41         51
           |          |          |          |          |          |
  1  MDNLRECINR KRRLLALPDV PETSDAFLSD LRHLYMCVAF CDQHKTTGDE SRFTNLELLD    60
 61  QDEALGAQRA FEAKHGIKGG SLGDVLDHEL KKVIEFTFTS GSLYIAEQRK RKTQADSIIV   120
121  CVSEGLNDFS VSHGVLDMGL VETGVNAVRD FCTQNGIPMK INQVGSTRTP TPISTCKISE   180
181  QITRQINSTI TERKMETVLA AIAIKPELKL TQKGCRPCKE LEDENILWMD PQFCEIDESP   240
241  PYRGGPYGNF LQELLLTTND VETNGKDREE VVKKILDNKA FTVESGECII TLPDKMTCFG   300
301  EQEKKRPATI DEVRTAGERF EQSVKPKTQR YGRLSDKWME LEKFIFTASK TEVDTFLSVG   360
361  TERLESVGVC VGALHRATTT RIIRPMIQGG KCWGMMFKTK SKMGDTRKEG YCHAIIFGKG   420
421  EDKSGQNKMT MMGKTVHWHL RVVKSKGDWM AQQLCANKSR IWEHDPELVT EGVTVLMTPF   480
481  SQKIATISRW RAMRLDSMFH VSSAWHHSPA CEAASAMLRK FVEIVHAINQ KRDWGVVGSM   540
541  EDMVKEVEEI GEHLQTACDF RVYNMCKALI QKIAVSTQ
```

Molecular weight: 65336.10
Theoretical pI: 6.94

Figure 3: ISA1mta Nucleotide Sequence

```
gcaaagatyg ctcaaatccc aaaaataata cagaaaacgt ataagagatg gccgataaag      60
gtatgactta ttcttttgat gtcagagaca acaccttggt tgtaagaaga tctaccgcta     120
ctaaaagtgg cattaagatc tcctacagag aggatcgagg aacatcactt ctccaaaagg     180
cattcgccgg gacagaagat gaattctggg tggagttaga tcaagatgtc tacgttgaca     240
aaaagattag aaaattcctg gaagaagaga aaatgaagga catgagcaca agagtgtctg     300
gagcagtggc agcagcaatt gaaagatcag ttgaatttga caatttctca aaagaagcag     360
cagctaacat tgaaatggct ggtgtagatg atgaagaagc tggaggaagt ggtctggtag     420
acaacagaag gaagaacaaa ggggtctcaa acatggccta caatctgtct ctattcatag     480
ggatggtgtt tcctgctctc actactttct tcagtgctat cctatcagaa ggtgaaatga     540
gcatctggca aaatggacaa gcaatcatca gaattctggc actggcagat gaagacggaa     600
agagacaaac aagaacagga ggacagaggg tggacatggc tgatgtaacc aagctgaacg     660
tagtcacggc taacgggaaa gtcaagcaag ttgaagtaaa cttgaacgat ctcaaagcag     720
cattcaggca gagtagacct aaaagatcgg actacagaaa agggcaaggt tccaaggcta     780
cagaatcaag catctccaac caatgtatgg cactgattat gaaatctgtg ctgtcagcag     840
accaactttt tgctccggga gtgaagatga tgaggacgaa cggtttcaat gcgtcgtaca     900
caacactggc agaaggggca aacattccga gcaagtacct aagacacatg aggaactgcg     960
gaggagtagc tctggacctg atgggaatga agaggatcaa aaactcacct gaaggagcca    1020
agtctaagat cttttccatc atccagaaga aagtaagagg aagatgtcgc acagaggagc    1080
aacgcctcct gactagcgca ctgaaaatca gcgacggtga aaacaagttc cagagaatca    1140
tggacactct atgtacaagc ttcctgattg accctccaag aactaccaaa tgcttcattc    1200
cacctatttc cagtctcatg atgtacatcc aagaaggcaa ctctgtactg gcaatggatt    1260
tcatgaaaaa cggagaggac gcctgcaaga tctgcagaga agccaaactg aaagtggggg    1320
taaacagtac gttcacaatg tcagtagcta gaacatgcgt tgcagtgtca atggttgcaa    1380
cagcttttg ttctgcagat atcatcgaga atgcagtgcc tggttccgaa aggtacagat    1440
ccaacatcaa ggctaacaca accaaaccaa aaaggactc cacttacaca attcaaggac    1500
ttagattgtc taacgtgagg tatgaagcaa gacctgaaac atcacaaagc aacacagaca    1560
gaagttggca agtgaacgtg actgacagct tcggaggact tgctgtgttc aaccaagggg    1620
caattagaga aatgctagga gacggaacat cagagacaac tagtgtgaac gtcagagccc    1680
tggtgaagag aattctgaaa tcagcttcag agaggagtgc aagagctgta aagacattta    1740
tggtgggaga acaagggaaa tcagctattg ttatctctgg tgtgggactg ttctctattg    1800
actttgaagg ggtagaggaa gcggaaagga taactgacat gacacctgaa attgagtttg    1860
acgaggacga cgaggaagag gaagacattg acatttagag tgacaattat gtaacttttct    1920
aattacccta tattgtttga atatataatg aaactattgt gtgttaaagg ttgtgggttt    1980
gattattaaa tttaaattga aacggtattg acgatatt                            2018
```

Figure 4: ISA1mta Amino Acid Sequence

```
        1          11         21         31         41         51
        |          |          |          |          |          |

1  MADKGMTYSF DVRDNTLVVR RSTATKSGIK ISYREDRGTS LLQKAFAGTE DEFWVELDQD   60

61  VYVDKKIRKF LEEEKMKDMS TRVSGAVAAA IERSVEFDNF SKEAAANIEM AGVDDEEAGG  120

121  SGLVDNRRKN KGVSNMAYNL SLFIGMVFPA LTTFFSAILS EGEMSIWQNG QAIIRILALA  180

181  DEDGKRQTRT GGQRVDMADV TKLNVVTANG KVKQVEVNLN DLKAAFRQSR PKRSDYRKGQ  240

241  GSKATESSIS NQCMALIMKS VLSADQLFAP GVKMMRTNGF NASYTTLAEG ANIPSKYLRH  300

301  MRNCGGVALD LMGMKRIKNS PEGAKSKIFS IIQKKVRGRC RTEEQRLLTS ALKISDGENK  360

361  FQRIMDTLCT SFLIDPPRTT KCFIPPISSL MMYIQEGNSV LAMDFMKNGE DACKICREAK  420

421  LKVGVNSTFT MSVARTCVAV SMVATAFCSA DIIENAVPGS ERYRSNIKAN TTKPKKDSTY  480

481  TIQGLRLSNV RYEARPETSQ SNTDRSWQVN VTDSFGGLAV FNQGAIREML GDGTSETTSV  540

541  NVRALVKRIL KSASERSARA VKTFMVGEQG KSAIVISGVG LFSIDFEGVE EAERITDMTP  600

601  EIEFDEDDEE EEDIDI
```

Molecular weight: 68050.47

Theoretical pI: 8.20

Figure 5: ISA3mx Nucleotide Sequence

```
atgtctggat ttaacctcga ggtaatggtg ccggaacaag gaggaaaagt ggtcttcagc      60
cttactgaaa cggggtcatg tgtctcgttt tacggagatg atgaaccagg tgaagggtcc     120
tgcgaacttg cctctgaaaa catggatttt ccaagttgtc ctctggggaa tggagatgac     180
ttctgtctgt cgctggcgct aagcacaatg agatggtctg ggatgaccaa gagaaacaac     240
ttcatggaca gattcattgg aagttttgtt cactgtacac cagtgatgat ctggtcgtat     300
ggaaatttgt ccaagaaaag ccatcacaaa atggtttgcc acacttgccc agacgagtac     360
aagttcagtg acaaggacga gatgcaggga tactatgagg gatgtctaga ggcttctact     420
gacatttttcc ttgatgaact tgctactgtt gttacaggtg gcttctttcc tgtcggactc     480
aaaggttcct ggggaggatg gtacctcaag tacgtcaggt atgctggacc tcttgcggga     540
tcaagtggat tcattgtcaa tcaacgattc tacgacagag cccaaaacaa gactggatcc     600
agggttgtat ccatggttga aatggacgga gacggcttat cgttcatcta cgaagagcct     660
agcgtctacc atagtgatgg gtgcactggg tcagcagcga ggttctggaa acgggatcac     720
aatgagagag ctggagttga gcttagggct ggacttcact tcagaatgtg attggttgaa     780
aacttgttat gtaaacaaga attttgtgtt tttgtcagaa aaagaaattg ctgtaaacat     840
ggaagttgaa aaattcattt gtaatgagaa ctaaagatgt ctttgtgttc aaattcttaac    900
taatgacaat atatgaaata tgtcgtacat ggtgttgatg ataatttttta aaacgaaaag    960
gagaattttt actaaaataa aaaaaaaata aaaaaaaaaa aaaagaaaaa aaaaaaaaaa    1020
aaaaaaagtc gacatcgata cgcgtggtca                                     1050
```

Figure 6a: Predicted Amino Acid Sequence of unspliced (M1) product of ISA3mx

MSGFNLEVMVPEQGGKVVFSLTETGSCVSFYGDDEPGEGSCELASENMDFPSCPLGNGDD 60

FCLSLALSTMRWSGMTKRNNFMDRFIGSFVHCTPVMIWSYGNLSKKSHHKMVCHTCPDEY 120

KFSDKDEMQGYYEGCLEASTDIFLDELATVVTGGFFPVGLKGSWGGWYLKYVRYAGLAG 180

SSGFIVNQRFYDRAQNKTGSRVVSMVEMDGDGLSFIYEKPSVYHSDGCTGSAARFWKRDH 240

NERAGVELRAGLHFRM 256

Molecular weight: 28,498

Theoetical pI: 5.38

Figure 6b: Predicted Amino Acid Sequence of spliced (M2) product of ISA3mx

MSGFNLEVMVPEQGGKVVFSLTETGSCVSFYGDDEPGGFFPVGLKGSWGGSYLKYVRYAG 60

PLAGSSGFIVNQRFYDRAQNKTGSRVVSMVEMDGDGLSFIYEKPSVYHSDGCTGSAARFW 120

KRDHNERAGVELRAGLHFRM 140

Molecular weight: 15,357

Theoetical pI: 6.82

Figure 6c: Predicted Amino Acid sequence of spliced (M3) product of ISA3mx

MNLLLLLQVASFLSDSKVPGEDGTSSTSGMLDLLRDQVDSLSINDSTTEPKTRLDPGLYP 60

WLKWTETAYRSSTRSLASTIVMGALGQQRGSGNGITMRELELSLGLDFTSECDWLKTCYV 120

NKNFVFLSEKEIAVNMEVEKFICNEN 147

Molecular weight: 14,888

Theoretical pI: 4.65

Figure 7: ISA4ha Nucleotide Sequence

```
cagtcgtcta tgtcttagaa accatcctga caccacctgg ataggtgact cccgaagcga    60
tcaatcaagg gtgaaccaac agtctcttga tctggttaca aacttcaagg gaattctaca   120
agccaagaac gggaatggtc tcatgaagca gatgagcgga aggttcccaa gtgattggta   180
ccaacctact acaaagtata ggattctata cattggtaca aacgactgca ctgagggccc   240
taacgacgtg atcataccga cgtcaatgac actagacaat gtggcaaggg acctgtacct   300
gggagcatgt cgaggagatg taagagtgac accaaccttc gtgggagcag ctgagcttgg   360
actgattggg agaacagatg ccttaacagg attttctgta aaggtgctga ctttcaacaa   420
ccctactatt gtagtagttg gactaaatgg aatgtcagga atctacaagg tctgcattgc   480
tgcctcttct ggaaacgtag gcggagtcaa cttggtgaac ggatgcggat acttcagcgc   540
tcctctgaga ttcgacaact tcaaaggaca gatctacgtg tcagacacct ttgaagtcag   600
aggaacaaag aacaaatgtg tcatacttag atcttctagc aatgctcctt tgtgtacaca   660
tatcaaaaga aacattgagt tggatgagta cgttgacaca ccaaacactg ggggcgtata   720
tccttctgat gggtttgatt ctcttcacgg ctctgcttcg attagaactt ttttaacaga   780
ggcactgaca tgtccaggtg tagattggga cagaattgat gcagcttcat gcgagtatga   840
cagttgtcct aaacttgtga aagaatttga ccaaacaggg ctcggaaaca cagatactca   900
aataatgaga gagctagaag cacaaaagga gatgattggt aaacttggca gaaacattac   960
agacgtaaac aacagagtag atgctattcc accacagctt agcaacatct tcatctctat  1020
gggagtggca ggt                                                     1033
```

Figure 8: ISA4ha Amino Acid Sequence

```
         1          11         21         31         41         51
         |          |          |          |          |          |
   1  SRLCLRNHPD TTWIGDSRSD QSRVNQQSLD LVTNFKGILQ AKNGNGLMKQ MSGRFPSDWY    60
  61  QPTTKYRILY IGTNDCTEGP NDVIIPTSMT LDNVARDLYL GACRGDVRVT PTFVGAAELG   120
 121  LIGRTDALTG FSVKVLTFNN PTIVVVGLNG MSGIYKVCIA ASSGNVGGVN LVNGCGYFSA   180
 181  PLRFDNFKGQ IYVSDTFEVR GTKNKCVILR SSSNAPLCTH IKRNIELDEY VDTPNTGGVY   240
 241  PSDGFDSLHG SASIRTFLTE ALTCPGVDWD RIDAASCEYD SCPKLVKEFD QTGLGNTDTQ   300
 301  IMRELEAQKE MIGKLGRNIT DVNNRVDAIP PQLSNIFISM GVAG
```

Molecular Weight: 37,437

Theoretical pI: 5.38

SEQUENCE LISTING

<160> NUMBER OF SEQ ID NOS: 10

<210> SEQ ID NO 1
<211> LENGTH: 1821
<212> TYPE: DNA
<213> ORGANISM: Infectious Salmon Anaemia Virus

<400> SEQUENCE: 1

```
caagatggat aacctccgtg aatgcataaa ccgcaaaaga agactacttg ccttaccaga       60
tgttcctgaa acttcggatg cctttctaag tgatttgaga catctataca tgtgtgttgc      120
tttctgtgat caacacaaaa ccactggaga cgaatcaaga ttcaccaacc tggaattact      180
tgaccaagat gaagcactag gtgcccaaag agcttttgaa gccaaacatg aataaaagg       240
aggttcttta ggagacgttc ttgaccatga actgaaaaag gtcattgaat ttacttttac      300
ttctggaagt ttgtatattg ccgaacaaag aaaaagaaag actcaagcag actcaataat      360
tgtgtgcgtt tcagaaggac ttaacgactt cagcgtatca cacggagtgc tagacatggg      420
acttgtggaa acaggggtga atgcagtaag agatttctgc acacaaaacg gaataccaat      480
gaagataaat caggtaggat ccacgagaac accaacaccg atcagcacat gcaaaatctc      540
tgaacaaata acacgacaga taaacagtac aattactgaa aggaaaatgg aaacagtact      600
ggcagcaatc gcaattaaac cagaactcaa actaactcag aaaggatgca gaccttgtaa      660
agaactagaa gatgaaaata ttctgtggat ggaccctcaa ttctgtgaaa ttgatgaaag      720
ttttccttac agaggagggc catacgggaa cttcctgcaa gaattgctgc ttacaaccaa      780
cgacgtagag accaacggga agacagaga agaagtagta aagaagatac tggataacaa      840
ggcgttcacc gttgaaagtg gtgaatgcat aataacactt ccagacaaaa tgacttgttt      900
cggagaacag gagaagaaga gaccagcaac aatagacgaa gtgagaaccg caggagaaag      960
gtttgaacag agtgttaaac cgaaaaccca agatatggaa aggttatcag acaaatggat     1020
ggagcttgaa aagtttatct ttactgcaag caaaacagaa gtggatactt ccttctctgt     1080
agggaccgaa agacttgagt cggttggagt gtgtgtcgga gctttacaca gagcgaccac     1140
aaccaggata attagaccta tgattcaagg agggaaatgt tgggggatga tgttcaaaac     1200
aaagtccaaa atgggagaca cgaggaagga aggatactgt cacgcaatca ttttcggaaa     1260
aggggaagat aaatcaggac aaaacaagat gacaatgatg gggaaaacag tacattggca     1320
tctaagagta gttaagtcta aaggagactg gatggcgcaa caactctgtg caaacaaaag     1380
cagaatatgg gaacatgacc ctgagctagt aacagaagga gtgacagttc taatgacgcc     1440
tttttctcag aaaattgcca ccattagtag atggagggca atgaggttag acagcatgtt     1500
tcatgttttct agtgcctggc atcattcacc tgcgtgtgaa gctgcatcgg caatgctgag     1560
aaagtttgtg gagatagtac atgccatcaa ccagaaaaga gattgggggtg ttgtggggag     1620
tatggaggac atggtgaagg aagtggagga aataggggag cacttgcaga cggcatgtga     1680
ttttagagtt tacaacatgt gcaaagcctt gattcagaaa attgcagtca gtacccaatg     1740
agtggttatt tacttgtaaa ttgttgtgtg tttgacgata tgtatttgtc gacgcggccg     1800
cggtcgacgc ggccgcgaat t                                              1821
```

<210> SEQ ID NO 2
<211> LENGTH: 578
<212> TYPE: PRT
<213> ORGANISM: Infectious Salmon Anaemia Virus -continued

```
<400> SEQUENCE: 2

Met Asp Asn Leu Arg Glu Cys Ile Asn Arg Lys Arg Arg Leu Leu Ala
1               5                   10                  15

Leu Pro Asp Val Pro Glu Thr Ser Asp Ala Phe Leu Ser Asp Leu Arg
            20                  25                  30

His Leu Tyr Met Cys Val Ala Phe Cys Asp Gln His Lys Thr Thr Gly
        35                  40                  45

Asp Glu Ser Arg Phe Thr Asn Leu Glu Leu Leu Asp Gln Asp Glu Ala
    50                  55                  60

Leu Gly Ala Gln Arg Ala Phe Glu Ala Lys His Gly Ile Lys Gly Gly
65                  70                  75                  80

Ser Leu Gly Asp Val Leu Asp His Glu Leu Lys Lys Val Ile Glu Phe
                85                  90                  95

Thr Phe Thr Ser Gly Ser Leu Tyr Ile Ala Glu Gln Arg Lys Arg Lys
            100                 105                 110

Thr Gln Ala Asp Ser Ile Ile Val Cys Val Ser Glu Gly Leu Asn Asp
        115                 120                 125

Phe Ser Val Ser His Gly Val Leu Asp Met Gly Leu Val Glu Thr Gly
    130                 135                 140

Val Asn Ala Val Arg Asp Phe Cys Thr Gln Asn Gly Ile Pro Met Lys
145                 150                 155                 160

Ile Asn Gln Val Gly Ser Thr Arg Thr Pro Thr Pro Ile Ser Thr Cys
                165                 170                 175

Lys Ile Ser Glu Gln Ile Thr Arg Gln Ile Asn Ser Thr Ile Thr Glu
            180                 185                 190

Arg Lys Met Glu Thr Val Leu Ala Ala Ile Ala Ile Lys Pro Glu Leu
        195                 200                 205

Lys Leu Thr Gln Lys Gly Cys Arg Pro Cys Lys Glu Leu Glu Asp Glu
    210                 215                 220

Asn Ile Leu Trp Met Asp Pro Gln Phe Cys Glu Ile Asp Glu Ser Phe
225                 230                 235                 240

Pro Tyr Arg Gly Gly Pro Tyr Gly Asn Phe Leu Gln Glu Leu Leu Leu
                245                 250                 255

Thr Thr Asn Asp Val Glu Thr Asn Gly Lys Asp Arg Glu Glu Val Val
            260                 265                 270

Lys Lys Ile Leu Asp Asn Lys Ala Phe Thr Val Glu Ser Gly Glu Cys
        275                 280                 285

Ile Ile Thr Leu Pro Asp Lys Met Thr Cys Phe Gly Glu Gln Glu Lys
    290                 295                 300

Lys Arg Pro Ala Thr Ile Asp Glu Val Arg Thr Ala Gly Glu Arg Phe
305                 310                 315                 320

Glu Gln Ser Val Lys Pro Lys Thr Gln Arg Tyr Gly Arg Leu Ser Asp
                325                 330                 335

Lys Trp Met Glu Leu Glu Lys Phe Ile Phe Thr Ala Ser Lys Thr Glu
            340                 345                 350

Val Asp Thr Phe Leu Ser Val Gly Thr Glu Arg Leu Glu Ser Val Gly
        355                 360                 365

Val Cys Val Gly Ala Leu His Arg Ala Thr Thr Thr Arg Ile Ile Arg
    370                 375                 380

Pro Met Ile Gln Gly Gly Lys Cys Trp Gly Met Met Phe Lys Thr Lys
385                 390                 395                 400

Ser Lys Met Gly Asp Thr Arg Lys Glu Gly Tyr Cys His Ala Ile Ile
```

```
                    405                 410                 415
        Phe Gly Lys Gly Glu Asp Lys Ser Gly Gln Asn Lys Met Thr Met Met
                    420                 425                 430

Gly Lys Thr Val His Trp His Leu Arg Val Val Lys Ser Lys Gly Asp
                    435                 440                 445

Trp Met Ala Gln Gln Leu Cys Ala Asn Lys Ser Arg Ile Trp Glu His
                    450                 455                 460

Asp Pro Glu Leu Val Thr Gly Val Thr Val Leu Met Thr Pro Phe
        465                 470                 475                 480

Ser Gln Lys Ile Ala Thr Ile Ser Arg Trp Arg Ala Met Arg Leu Asp
                    485                 490                 495

Ser Met Phe His Val Ser Ser Ala Trp His His Ser Pro Ala Cys Glu
                    500                 505                 510

Ala Ala Ser Ala Met Leu Arg Lys Phe Val Glu Ile Val His Ala Ile
                    515                 520                 525

Asn Gln Lys Arg Asp Trp Gly Val Val Gly Ser Met Glu Asp Met Val
                    530                 535                 540

Lys Glu Val Glu Glu Ile Gly Glu His Leu Gln Thr Ala Cys Asp Phe
        545                 550                 555                 560

Arg Val Tyr Asn Met Cys Lys Ala Leu Ile Gln Lys Ile Ala Val Ser
                    565                 570                 575

Thr Gln

<210> SEQ ID NO 3
<211> LENGTH: 2018
<212> TYPE: DNA
<213> ORGANISM: Infectious Salmon Anaemia Virus

<400> SEQUENCE: 3
gcaaagatyg ctcaaatccc aaaaataata cagaaaacgt ataagagatg gccgataaag      60
gtatgactta ttcttttgat gtcagagaca cacccttggt tgtaagaaga tctaccgcta     120
ctaaaagtgg cattaagatc tcctacagag aggatcgagg aacatcactt ctccaaaagg     180
cattcgccgg gacagaagat gaattctggg tggagttaga tcaagatgtc tacgttgaca     240
aaaagattag aaaattcctg gaagaagaga aatgaagga catgagcaca agagtgtctg      300
gagcagtggc agcagcaatt gaaagatcag ttgaatttga caatttctca aaagaagcag     360
cagctaacat tgaaatggct ggtgtagatg atgaagaagc tggaggaagt ggtctggtag     420
acaacagaag gaagaacaaa ggggtctcaa acatggccta caatctgtct ctattcatag     480
ggatggtgtt tcctgctctc actactttct tcagtgctat cctatcagaa ggtgaaatga     540
gcatctggca aaatggacaa gcaatcatca gaattctggc actggcagat gaagacggaa     600
agagacaaac aagaacagga ggacagaggg tggacatggc tgatgtaacc aagctgaacg     660
tagtcacggc taacgggaaa gtcaagcaag ttgaagtaaa cttgaacgat ctcaaagcag     720
cattcaggca gagtagacct aaaagatcgg actacagaaa agggcaaggt tccaaggcta     780
cagaatcaag catctccaac caatgtatgg cactgattat gaaatctgtg ctgtcagcag     840
accaactttt tgctccggga gtgaagatga tgaggacgaa cggtttcaat gcgtcgtaca     900
caacactggc agaaggggca acattccga gcaagtacct aagacacatg aggaactgcg      960
gaggagtagc tctggaccctg atgggaatga gaggatcaa aaactcacct gaaggagcca    1020
agtctaagat cttttccatc atccagaaga agtaagagg aagatgtcgc acagaggagc    1080
aacgcctcct gactagcgca ctgaaaatca gcgacggtga aaacaagttc cagagaatca    1140
```

-continued

```
tggacactct atgtacaagc ttcctgattg accctccaag aactaccaaa tgcttcattc    1200
cacctatttc cagtctcatg atgtacatcc aagaaggcaa ctctgtactg gcaatggatt    1260
tcatgaaaaa cggagaggac gcctgcaaga tctgcagaga agccaaactg aaagtggggg    1320
taaacagtac gttcacaatg tcagtagcta gaacatgcgt tgcagtgtca atggttgcaa    1380 cagcttttg ttctgcagat atcatcgaga atgcagtgcc tggttccgaa aggtacagat     1440
ccaacatcaa ggctaacaca accaaaccaa aaaaggactc cacttacaca attcaaggac    1500
ttagattgtc taacgtgagg tatgaagcaa gacctgaaac atcacaaagc aacacagaca    1560
gaagttggca agtgaacgtg actgacagct tcggaggact tgctgtgttc aaccaagggg    1620
caattagaga aatgctagga gacgaacat cagagacaac tagtgtgaac gtcagagccc      1680
tggtgaagag aattctgaaa tcagcttcag agaggagtgc aagagctgta aagacattta    1740
tggtgggaga acaagggaaa tcagctattg ttatctctgg tgtgggactg ttctctattg     1800
actttgaagg ggtagaggaa gcggaaagga taactgacat gacacctgaa attgagtttg    1860
acgaggacga cgaggaagag gaagacattg acatttagag tgacaattat gtaactttct    1920
aattacccta tattgtttga atatataatg aaactattgt gtgttaaagg ttgtgggttt     1980
gattattaaa tttaaattga aacggtattg acgatatt                              2018
```

<210> SEQ ID NO 4
<211> LENGTH: 616
<212> TYPE: PRT
<213> ORGANISM: Infectious Salmon Anaemia Virus

<400> SEQUENCE: 4

Met Ala Asp Lys Gly Met Thr Tyr Ser Phe Asp Val Arg Asp Asn Thr
 1               5                  10                  15

Leu Val Val Arg Arg Ser Thr Ala Thr Lys Ser Gly Ile Lys Ile Ser
             20                  25                  30

Tyr Arg Glu Asp Arg Gly Thr Ser Leu Leu Gln Lys Ala Phe Ala Gly
         35                  40                  45

Thr Glu Asp Glu Phe Trp Val Glu Leu Asp Gln Asp Val Tyr Val Asp
     50                  55                  60

Lys Lys Ile Arg Lys Phe Leu Glu Glu Lys Met Lys Asp Met Ser
 65                  70                  75                  80

Thr Arg Val Ser Gly Ala Val Ala Ala Ile Glu Arg Ser Val Glu
             85                  90                  95

Phe Asp Asn Phe Ser Lys Glu Ala Ala Ala Asn Ile Glu Met Ala Gly
            100                 105                 110

Val Asp Glu Glu Ala Gly Gly Ser Gly Leu Val Asp Asn Arg Arg
            115                 120                 125

Lys Asn Lys Gly Val Ser Asn Met Ala Tyr Asn Leu Ser Leu Phe Ile
        130                 135                 140

Gly Met Val Phe Pro Ala Leu Thr Thr Phe Phe Ser Ala Ile Leu Ser
145                 150                 155                 160

Glu Gly Glu Met Ser Ile Trp Gln Asn Gly Gln Ala Ile Ile Arg Ile
                165                 170                 175

Leu Ala Leu Ala Asp Glu Asp Gly Lys Arg Gln Thr Arg Thr Gly Gly
            180                 185                 190

Gln Arg Val Asp Met Ala Asp Val Thr Lys Leu Asn Val Val Thr Ala
        195                 200                 205

Asn Gly Lys Val Lys Gln Val Glu Val Asn Leu Asn Asp Leu Lys Ala

-continued

```
            210                 215                 220
Ala Phe Arg Gln Ser Arg Pro Lys Arg Ser Asp Tyr Arg Lys Gly Gln
225                 230                 235                 240

Gly Ser Lys Ala Thr Glu Ser Ser Ile Ser Asn Gln Cys Met Ala Leu
                245                 250                 255

Ile Met Lys Ser Val Leu Ser Ala Asp Gln Leu Phe Ala Pro Gly Val
                260                 265                 270

Lys Met Arg Thr Asn Gly Phe Asn Ala Ser Tyr Thr Thr Leu Ala
                275                 280                 285

Glu Gly Ala Asn Ile Pro Ser Lys Tyr Leu Arg His Met Arg Asn Cys
            290                 295                 300

Gly Gly Val Ala Leu Asp Leu Met Gly Met Lys Arg Ile Lys Asn Ser
305                 310                 315                 320

Pro Glu Gly Ala Lys Ser Lys Ile Phe Ser Ile Ile Gln Lys Lys Val
                325                 330                 335

Arg Gly Arg Cys Arg Thr Glu Glu Gln Arg Leu Leu Thr Ser Ala Leu
                340                 345                 350

Lys Ile Ser Asp Gly Glu Asn Lys Phe Gln Arg Ile Met Asp Thr Leu
            355                 360                 365

Cys Thr Ser Phe Leu Ile Asp Pro Pro Arg Thr Thr Lys Cys Phe Ile
            370                 375                 380

Pro Pro Ile Ser Ser Leu Met Met Tyr Ile Gln Glu Gly Asn Ser Val
385                 390                 395                 400

Leu Ala Met Asp Phe Met Lys Asn Gly Glu Asp Ala Cys Lys Ile Cys
                405                 410                 415

Arg Glu Ala Lys Leu Lys Val Gly Val Asn Ser Thr Phe Thr Met Ser
                420                 425                 430

Val Ala Arg Thr Cys Val Ala Val Ser Met Val Ala Thr Ala Phe Cys
                435                 440                 445

Ser Ala Asp Ile Ile Glu Asn Ala Val Pro Gly Ser Glu Arg Tyr Arg
            450                 455                 460

Ser Asn Ile Lys Ala Asn Thr Thr Lys Pro Lys Lys Asp Ser Thr Tyr
465                 470                 475                 480

Thr Ile Gln Gly Leu Arg Leu Ser Asn Val Arg Tyr Glu Ala Arg Pro
                485                 490                 495

Glu Thr Ser Gln Ser Asn Thr Asp Arg Ser Trp Gln Val Asn Val Thr
            500                 505                 510

Asp Ser Phe Gly Gly Leu Ala Val Phe Asn Gln Gly Ala Ile Arg Glu
            515                 520                 525

Met Leu Gly Asp Gly Thr Ser Glu Thr Thr Ser Val Asn Val Arg Ala
            530                 535                 540

Leu Val Lys Arg Ile Leu Lys Ser Ala Ser Glu Arg Ser Ala Arg Ala
545                 550                 555                 560

Val Lys Thr Phe Met Val Gly Glu Gln Gly Lys Ser Ala Ile Val Ile
                565                 570                 575

Ser Gly Val Gly Leu Phe Ser Ile Asp Phe Glu Gly Val Glu Glu Ala
                580                 585                 590

Glu Arg Ile Thr Asp Met Thr Pro Glu Ile Glu Phe Asp Glu Asp
            595                 600                 605

Glu Glu Glu Glu Asp Ile Asp Ile
610                 615
```

<210> SEQ ID NO 5

```
<211> LENGTH: 1050
<212> TYPE: DNA
<213> ORGANISM: Infectious Salmon Anaemia Virus

<400> SEQUENCE: 5
atgtctggat ttaacctcga ggtaatggtg ccggaacaag gaggaaaagt ggtcttcagc      60
cttactgaaa cggggtcatg tgtctcgttt tacggagatg atgaaccagg tgaaggtcc     120 tgcgaacttg cctctgaaaa catggatttt ccaagttgtc ctctgggaa tggagatgac      180 ttctgtctgt cgctggcgct aagcacaatg agatggtctg ggatgaccaa gagaaacaac    240 tcatggaca gattcattgg aagttttgtt cactgtacac cagtgatgat ctggtcgtat      300
ggaaatttgt ccaagaaaag ccatcacaaa atggtttgcc acacttgccc agacgagtac    360
aagttcagtg acaaggacga gatgcaggga tactatgagg gatgtctaga ggcttctact    420 gacatttttcc ttgatgaact tgctactgtt gttacaggtg gcttctttcc tgtcggactc    480
aaaggttcct ggggaggatg gtacctcaag tacgtcaggt atgctggacc tcttgcggga    540
tcaagtggat tcattgtcaa tcaacgattc tacgacagag cccaaaacaa gactggatcc    600
agggttgtat ccatggttga atggacggga acggcttat cgttcatcta cgagaagcct     660
agcgtctacc atagtgatgg gtgcactggg tcagcagcga ggttctggaa acgggatcac    720
aatgagagag ctggagttga gcttagggct ggacttcact tcagaatgtg attggttgaa    780
aacttgttat gtaaacaaga attttgtgtt tttgtcagaa aaagaaattg ctgtaaacat    840
ggaagttgaa aaattcattt gtaatgagaa ctaaagatgt ctttgtgttc aaatttttaac   900 taatgacaat atatgaaata tgtcgtacat ggtgttgatg ataattttta aaacgaaaag   960 gagaatttt actaaaataa aaaaaaaata aaaaaaaaa aaaagaaaaa aaaaaaaaa      1020 aaaaaaagtc gacatcgata cgcgtggtca                                    1050

<210> SEQ ID NO 6
<211> LENGTH: 256
<212> TYPE: PRT
<213> ORGANISM: Infectious Salmon Anaemia Virus

<400> SEQUENCE: 6

Met Ser Gly Phe Asn Leu Glu Val Met Val Pro Glu Gln Gly Gly Lys
  1               5                  10                  15

Val Val Phe Ser Leu Thr Glu Thr Gly Ser Cys Val Ser Phe Tyr Gly
                 20                  25                  30

Asp Asp Glu Pro Gly Glu Gly Ser Cys Glu Leu Ala Ser Glu Asn Met
             35                  40                  45

Asp Phe Pro Ser Cys Pro Leu Gly Asn Gly Asp Asp Phe Cys Leu Ser
         50                  55                  60

Leu Ala Leu Ser Thr Met Arg Trp Ser Gly Met Thr Lys Arg Asn Asn
 65                  70                  75                  80

Phe Met Asp Arg Phe Ile Gly Ser Phe Val His Cys Thr Pro Val Met
                 85                  90                  95

Ile Trp Ser Tyr Gly Asn Leu Ser Lys Lys Ser His His Lys Met Val
                100                 105                 110

Cys His Thr Cys Pro Asp Glu Tyr Lys Phe Ser Asp Lys Asp Glu Met
            115                 120                 125

Gln Gly Tyr Tyr Glu Gly Cys Leu Glu Ala Ser Thr Asp Ile Phe Leu
        130                 135                 140

Asp Glu Leu Ala Thr Val Val Thr Gly Gly Phe Phe Pro Val Gly Leu
145                 150                 155                 160
```

```
Lys Gly Ser Trp Gly Gly Trp Tyr Leu Lys Tyr Val Arg Tyr Ala Gly
            165                 170                 175

Pro Leu Ala Gly Ser Ser Gly Phe Ile Val Asn Gln Arg Phe Tyr Asp
            180                 185                 190

Arg Ala Gln Asn Lys Thr Gly Ser Arg Val Val Ser Met Val Glu Met
            195                 200                 205

Asp Gly Asp Gly Leu Ser Phe Ile Tyr Glu Lys Pro Ser Val Tyr His
            210                 215                 220

Ser Asp Gly Cys Thr Gly Ser Ala Ala Arg Phe Trp Lys Arg Asp His
225                 230                 235                 240

Asn Glu Arg Ala Gly Val Glu Leu Arg Ala Gly Leu His Phe Arg Met
            245                 250                 255

<210> SEQ ID NO 7
<211> LENGTH: 140
<212> TYPE: PRT
<213> ORGANISM: Infectious Salmon Anaemia Virus

<400> SEQUENCE: 7

Met Ser Gly Phe Asn Leu Glu Val Met

```
Met Arg Glu Leu Glu Leu Ser Leu Gly Leu Asp Phe Thr Ser Glu Cys
            100                 105                 110
Asp Trp Leu Lys Thr Cys Tyr Val Asn Lys Asn Phe Val Phe Leu Ser
        115                 120                 125
Glu Lys Glu Ile Ala Val Asn Met Glu Val Glu Lys Phe Ile Cys Asn
    130                 135                 140
Glu Asn
145

<210> SEQ ID NO 9
<211> LENGTH: 1033
<212> TYPE: DNA
<213> ORGANISM: Infectious Salmon Anaemia Virus

<400> SEQUENCE: 9
cagtcgtcta tgtcttagaa accatcctga caccacctgg ataggtgact cccgaagcga      60
tcaatcaagg gtgaaccaac agtctcttga tctggttaca acttcaagg gaattctaca     120
agccaagaac gggaatggtc tcatgaagca gatgagcgga aggttcccaa gtgattggta     180
ccaacctact acaaagtata ggattctata cattggtaca aacgactgca ctgagggccc     240
taacgacgtg atcataccga cgtcaatgac actagacaat gtggcaaggg acctgtacct     300
gggagcatgt cgaggagatg taagagtgac accaaccttc gtgggagcag ctgagcttgg     360
actgattggg agaacagatg ccttaacagg attttctgta aggtgctga cttttcaacaa     420
ccctactatt gtagtagttg gactaaatgg aatgtcagga atctacaagg tctgcattgc     480
tgcctcttct ggaaacgtag gcggagtcaa cttggtgaac ggatgcggat acttcagcgc     540
tcctctgaga ttcgacaact tcaaaggaca gatctacgtg tcagacacct ttgaagtcag     600
aggaacaaag aacaaatgtg tcatacttag atcttctagc aatgctcctt tgtgtacaca     660
tatcaaaaga aacattgagt tggatgagta cgttgacaca ccaaacactg ggggcgtata     720
tccttctgat gggtttgatt ctcttcacgg ctctgcttcg attagaactt ttttaacaga     780
ggcactgaca tgtccaggtg tagattggga cagaattgat gcagcttcat gcgagtatga     840
cagttgtcct aaacttgtga agaatttga ccaaacaggg ctcggaaaca cagatactca     900
aataatgaga gagctagaag cacaaaagga gatgattggt aaacttggca gaaacattac     960
agacgtaaac aacagagtag atgctattcc accacagctt agcaacatct tcatctctat    1020
gggagtggca ggt                                                        1033

<210> SEQ ID NO 10
<211> LENGTH: 344
<212> TYPE: PRT
<213> ORGANISM: Infectious Salmon Anaemia Virus

<400> SEQUENCE: 10

Ser Arg Leu Cys Leu Arg Asn His Pro Asp Thr Thr Trp Ile Gly Asp
  1               5                  10                  15
Ser Arg Ser Asp Gln Ser Arg Val Asn Gln Gln Ser Leu Asp Leu Val
             20                  25                  30
Thr Asn Phe Lys Gly Ile Leu Gln Ala Lys Asn Gly Asn Gly Leu Met
         35                  40                  45
Lys Gln Met Ser Gly Arg Phe Pro Ser Asp Trp Tyr Gln Pro Thr Thr
     50                  55                  60
Lys Tyr Arg Ile Leu Tyr Ile Gly Thr Asn Asp Cys Thr Glu Gly Pro
 65                  70                  75                  80
```

```
Asn Asp Val Ile Ile Pro Thr Ser Met Thr Leu Asp Asn Val Ala Arg
             85              90                  95

Asp Leu Tyr Leu Gly Ala Cys Arg Gly Asp Val Arg Val Thr Pro Thr
            100             105             110

Phe Val Gly Ala Ala Glu Leu Gly Leu Ile Gly Arg Thr Asp Ala Leu
            115             120             125

Thr Gly Phe Ser Val Lys Val Leu Thr Phe Asn Asn Pro Thr Ile Val
            130             135             140

Val Val Gly Leu Asn Gly Met Ser Gly Ile Tyr Lys Val Cys Ile Ala
145             150             155             160

Ala Ser Ser Gly Asn Val Gly Gly Val Asn Leu Val Asn Gly Cys Gly
            165             170             175

Tyr Phe Ser Ala Pro Leu Arg Phe Asp Asn Phe Lys Gly Gln Ile Tyr
            180             185             190

Val Ser Asp Thr Phe Glu Val Arg Gly Thr Lys Asn Lys Cys Val Ile
            195             200             205

Leu Arg Ser Ser Ser Asn Ala Pro Leu Cys Thr His Ile Lys Arg Asn
    210             215             220

Ile Glu Leu Asp Glu Tyr Val Asp Thr Pro Asn Thr Gly Gly Val Tyr
225             230             235             240

Pro Ser Asp Gly Phe Asp Ser Leu His Gly Ser Ala Ser Ile Arg Thr
            245             250             255

Phe Leu Thr Glu Ala Leu Thr Cys Pro Gly Val Asp Trp Asp Arg Ile
            260             265             270

Asp Ala Ala Ser Cys Glu Tyr Asp Ser Cys Pro Lys Leu Val Lys Glu
            275             280             285

Phe Asp Gln Thr Gly Leu Gly Asn Thr Asp Thr Gln Ile Met Arg Glu
            290             295             300

Leu Glu Ala Gln Lys Glu Met Ile Gly Lys Leu Gly Arg Asn Ile Thr
305             310             315             320

Asp Val Asn Asn Arg Val Asp Ala Ile Pro Pro Gln Leu Ser Asn Ile
            325             330             335

Phe Ile Ser Met Gly Val Ala Gly
            340
```

NUCLEIC ACID AND AMINO ACID SEQUENCES OF INFECTIOUS SALMON ANAEMIA VIRUS AND THEIR USE AS VACCINES

This application is a divisional application of U.S. patent application Ser. No. 10/049,086 filed May 30, 2002, now U.S. Pat. No. 6,919,083, which is the National Stage of International Patent Application PCT/GB00/02976 filed on Aug. 7, 2000.

The present invention relates to a fish vaccine. More specifically the invention relates to a vaccine to protect salmon against infectious salmon anaemia virus.

Infectious salmon anaemia virus (ISAV) causes mortality of farmed Atlantic salmon. Typically aquaculture revenue is reduced by over 30%. Accordingly, there is a need for an effective vaccine against ISAV.

It is an object of the present invention to provide a vaccine to protect against ISAV.

According to the present invention there is provided a composition containing at least one nucleic acid sequence and/or at least one amino acid sequence, or a synthetically prepared analogue thereof or a substantially homologous sequence, wherein the composition is derived from or based upon infectious salmon anaemia virus and wherein at least one of said nucleotide and/or amino acid sequences does not cause salmon anaemia and is capable of being used as or to prepare a vaccine to ISAV.

A substantially homologous nucleic acid sequence is a sequence which can be transcribed and/or translated to provide an amino acid sequence which is substantially homologous to at least a part of an antigen of ISAV.

Preferably the substantially homologous amino acid is at least 70% homologous with a part of an antigen of ISAV which is capable of inducing an immune response.

More preferably the substantially homologous amino acid sequence is at least 80% homologous with a part of an antigen of ISAV and can induce an immune response.

Most preferably the substantially homologous amino acid sequence is at least 90% homologous with a part of an antigen of ISAV and can induce an immune response.

Suitably the amino acid sequence is chosen from the group comprising Sequences ID numbers 2, 4, 6, 7, 8 or 10 as herein described.

Alternatively the amino acid sequence may comprise at least one fragment of Sequence ID numbers 2, 4, 6, 7, 8 or 10.

Alternatively said amino acid sequence may be truncated from an amino acid sequence of Sequences ID numbers 2, 4, 6, 7, 8 or 10 as herein described, which can induce an immune response.

Preferably the substantially homologous nucleotide sequence is at least 60% homologous with a part of a nucleic acid sequence of an antigen of ISAV and the translation product thereof is capable of inducing an immune response.

Preferably the substantially homologous nucleotide sequence is at least 70% homologous with a part of a nucleic acid sequence of an antigen of ISAV, and the translation product of which is capable of inducing an immune response.

More preferably the substantially homologous nucleotide sequence is at least 80% homologous with a part of a nucleic acid sequence of an antigen of ISAV and the translation product of which is capable of inducing an immune response.

Most preferably the substantially homologous nucleotide sequence is at least 90% homologous to a part of a nucleic acid sequence of an antigen of ISAV, the translation product of which is capable of inducing an immune response.

Suitably the nucleotide sequences are chosen from the group comprising Sequence ID numbers 1, 3, 5 or 9 as herein described.

Alternatively, the invention provides for fragments of the sequences described in Sequence ID numbers 1, 3, 5 and 9 as herein described and wherein translation products of said fragments result in the induction of an immune response.

Additionally, the sequences may comprise a truncated form of the sequences given as 1, 3, 5 and 9.

The nucleotide sequence may be incorporated in a plasmid.

The nucleotide sequence may be incorporated in a suitable expression vector.

A further aspect of the present invention provides for the use of a sequence chosen from the group consisting of Sequence ID numbers 1 to 10, as described in the present invention in the preparation of a vaccine and/or therapeutic medicament for the protection of fish from infection with Infectious Salmon Anaemia virus.

Typical nucleic acid sequences are ISA2cd (previously referred to as p1.38), ISA1mta (previously referred to as p8.17), ISA3mx (previously referred to as p6.28) and ISA4ha.

Preferably the peptide sequences are transcribed and translated from either one, two or all of the nucleic acid sequences; ISA2cd, ISA1mta, ISA3mx or ISA4ha and are incorporated into a vaccination strategy aimed at inducing an immune response to a surface antigen of ISAV and thus infectious salmon anaemia virus itself.

The invention provides the use of nucleic acid sequences or peptide sequences as defined herein in the preparation of a vaccine for the protection of fish against ISAV.

The invention further provides a vaccine to protect fish against ISAV wherein the vaccine includes nucleic acid or peptide sequences as defined herein.

Characterisation of the Novel Sequences of the Invention

The accompanying figures describe the invention in more detail, wherein;

FIG. 1 is the nucleotide sequence of ISA2cd,

FIG. 2 is the amino acid sequence which is obtained from translation of the ISA2cd nucleic acid sequence listed in FIG. 1, FIG. 3 is the nucleotide sequence of ISA1mta, FIG. 4 is the amino acid sequence which is obtained following transcription of the nucleic acid sequence listed in FIG. 3, FIG. 5 is the exact nucleotide sequence of ISA3mx, FIG. 6a is the amino acid sequence (M1) which is translated from the unspliced nucleic acid sequence of ISA3mx shown in FIG. 5, FIG. 6b is the amino acid sequence (M2) which is translated from the spliced nucleic acid sequence of ISA3mx shown in FIG. 5, and FIG. 6c is the amino acid sequence (M3) which is translated from the unspliced nucleic acid sequence of ISA3mx as shown in FIG. 5.

FIG. 7 is the nucleotide sequence of ISA4ha (SEQ ID NO: 9).

FIG. 8 is the amino acid sequence of ISA4ha (SEQ ID NO: 10).

In addition, information detailing the specific molecular weight (MW) and theoretical isoelectric focusing points (pI) is given at the foot of the respective amino acid sequence listings.

The nucleotide and amino acid sequences shown in the figures are further represented in the accompanying Patent-In generated sequence listings wherein;

Sequence ID number 1 is the nucleotide sequence of ISA2cd, as shown on FIG. 1,

Sequence ID Number 2 is the amino acid sequence of the ISA2cd, as shown in FIG. 2, Sequence ID number 3 is the nucleotide sequence of ISA1mta, as shown on FIG. 3, Sequence ID number 4 is the amino acid sequence of ISA1mta, as shown on FIG. 4, Sequence ID number 5 is the nucleotide sequence of ISA3mx, as shown on FIG. 5, Sequence ID number 6 is the predicted amino acid sequence of unspliced product of ISA3mx, as shown in FIG. 6a, Sequence ID number 7 is the predicted amino acid sequence of spliced ISA3mx, as shown in FIG. 6b, Sequence ID number 8 is the predicted amino acid sequence of spliced ISA3mx, as shown in FIG. 6c, Sequence ID number 9 is the nucleotide sequence of ISA4ha, as previously shown in FIG. 7, and Sequence ID number 10 is the amino acid sequence of ISA4ha, as previously shown in FIG. 8.

The genetic sequences shown for ISA1mta and ISA2cd and the unspliced and spliced genetic sequences for ISA3mx have been derived from cloned cDNA wherein the cDNA clones were derived from infectious salmon anaemia virus (ISAV) genomic material. The cloned material was sequenced from the 5' end and the 3' end insertion sites using overlapping amplicons to produce a contig.

Veracity of the contig was confirmed by Reverse Transcriptase Polymerase Chain Reaction amplification (RT-PCR) of appropriate sized amplicons from ISAV infected salmon tissue and tissue cultures. Such amplicons were however obtained from uninfected control material, indicating that the genetic material was of ISAV origin.

The open reading frames (ORFs) were completed by rapid amplification of cDNA ends (RACE) from the incomplete sequence from virus-infected tissue culture. Corrections were made for the in vivo transcribed mRNA that were not apparent from the originally cloned cDNAs.

The ORF from ISA2cd does not have any significant homology at the nucleotide or amino acid sequence with previous submissions to databases accessible by BLAST. However, proteins with similar molecular weights (Mw) and isoelectric points (pI) include 14 viral proteins in the Swiss-Prot database such as Hemagglutinin-Neuraminidase.

The ORF from ISA1mta is also without any significant homology to previously characterised proteins submitted to the BLAST searchable databases. However it is of interest that it has molecular weight and isoelectric point characteristics (68–69 kDa and pI 8.2) that are nearly identical to one of the most predominant viral proteins identified by two dimensional electrophoresis. The protein appears to be integrally associated with the membranes of the ISAV infected tissue cultures. If the ORF yields such a protein it would be considered valuable in any vaccination strategy to reduce the level of ISAV infection in any salmonoid species.

Further, in the sequences shown for ISA3mx, the unspliced ORF (the basis for predicted amino acid sequence M1) does not have any significant homology at the nucleotide or amino acid sequence level with the previous submission to databases accessible by BLAST. However, proteins with similar molecular weights and isoelectric focusing points include several viral coat and envelope proteins listed in the Swiss-Prot database. Both the predicted M1 and M2 proteins (obtained from ORF's following splicing of the nucleotide sequence) are predicted to be membrane associated proteins and if the ORFs encoded by ISA3mx yield such proteins it would be considered valuable in any vaccination strategy to reduce the level of ISAV infection in any salmonid species.

The predicted protein translation of M3 (shown in FIG. 6c and accompanying sequence listing) shows homology to a paromyxovirus fusion protein associated with the cell membrane and thought to be involved in cell adhesion. In view of this exhibited homology, M3 is potentially valuable in any vaccination strategy aimed at reducing the level of ISAV infection in any salmonid species.

The further sequence relating to ISA4ha nucleotide sequence was obtained by means of the following procedure. The ISA4ha protein was detected by polyclonal antibodies following hybridisation. The protein is found to occur in two alternative forms. These two alternative forms are of different sizes, and can be seen where the proteins are cultured on different cell lines, for example shc and chse.

As these two alternate forms were both detectable by antibody and varied in size depending on how it was grown, the protein is potentially a good candidate for virulence.

The protein was isolated and sequenced, resulting in a 24 amino acid fragment being produced. When this sequence was submitted, to BLAST searchable databases, it showed similarities to sequences of British and Norwegian strains of ISAV.

Subsequently, primers were designed based on the amino acid sequence obtained, along with reference to the sequences known for the similar British and Norwegian strains.

The primers were then subsequently used in polymerase chain reaction to amplify the relevant DNA fragment, which was subsequently sequenced and translated into amino acid coding.

The open reading frame listings obtained in the present invention, have particular commercial value for the following reasons:

1. There is sufficient reason to believe that the nucleotide corresponding amino acid sequences are of ISAV origin. Therefore, their incorporation into nucleic acid vaccines may have an impact on the reduction of mortality of farmed Atlantic salmon caused by ISAV which as previously stated, can typically reduce aquaculture revenues by over 30%.

2. Characterisation of the gene product will lead to the identification of key elements in the pathogenesis of infection and to the design of more accurate diagnostic tests which will also aid in epidemiological studies documenting the dissemination of different strains of the disease.

The nucleotide sequences ISA1mta, ISA2cd, ISA3mx, ISA4ha and associated derivatives thereof when translated into protein sequences being composed of either identical or equivalent amino acids, should induce a response by the hosts immune system. This principle can be further expanded to use these proteins in diagnostics tests and vaccination procedures.

The invention claimed is:

1. A composition comprising an isolated polypeptide comprising the amino acid sequence of SEQ ID NO: 10.

2. A composition comprising an isolated and purified polynucleotide comprising the sequence of SEQ ID NO: 9.

3. A composition comprising an isolated and purified nucleic acid encoding the amino acid sequence of SEQ ID NO: 10.

4. The composition according to claim 2 wherein said nucleic acid sequence is incorporated in a plasmid.

5. The composition according to claim 4 wherein said plasmid is an expression vector.

6. An immunogenic composition comprising an expression vector wherein said expression vector contains nucleic acid with the sequence of SEQ ID NO: 9.

7. An immunogenic composition comprising an expression vector wherein said expression vector contains nucleic acid that encodes for a protein with the amino acid sequence of SEQ ID NO: 10.

8. A diagnostic kit comprising the composition of claim 1.

9. A diagnostic kit comprising the composition of claim 2.

10. A diagnostic kit comprising the composition of claim 3.

11. A cell comprising the composition of claim 5.

12. The composition according to claim 3 wherein said nucleic acid sequence is incorporated in a plasmid.

13. The composition according to claim 12 wherein said plasmid is an expression vector.

* * * * *